US006812208B2

(12) United States Patent
Gluckman et al.

(10) Patent No.: US 6,812,208 B2
(45) Date of Patent: *Nov. 2, 2004

(54) METHODS TO IMPROVE NEURAL OUTCOME

(75) Inventors: Peter D. Gluckman, Auckland (NZ); Christopher E. Williams, Auckland (NZ); Jian Guan, Auckland (NZ); Rita V. M. Krishnamurthi, Auckland (NZ)

(73) Assignee: NeuronZ Ltd., Auckland (NZ)

( * ) Notice: Subject to any disclaimer, the term of this patent is extended or adjusted under 35 U.S.C. 154(b) by 287 days.

This patent is subject to a terminal disclaimer.

(21) Appl. No.: 09/866,536

(22) Filed: May 24, 2001

(65) Prior Publication Data

US 2002/0035066 A1 Mar. 21, 2002

Related U.S. Application Data

(63) Continuation-in-part of application No. 08/907,918, filed on Aug. 11, 1997, now abandoned, which is a continuation of application No. 08/656,331, and a continuation-in-part of application No. PCT/NZ94/00143, filed on Dec. 20, 1994, now abandoned.

(30) Foreign Application Priority Data

| Dec. 23, 1993 | (NZ) | ............................................. 250572 |
| Mar. 14, 1994 | (NZ) | ............................................. 260091 |
| Jul. 22, 1994 | (NZ) | ............................................. 264070 |

(51) Int. Cl.$^7$ ............................................. C07K 5/083
(52) U.S. Cl. ........................................ 514/8; 530/331
(58) Field of Search ........................... 514/18; 530/331

(56) References Cited

U.S. PATENT DOCUMENTS

| 4,906,614 | A |   | 3/1990  | Giertz ............................ 514/18 |
| 5,106,832 | A |   | 4/1992  | Froesch et al. ................. 514/3  |
| 5,273,961 | A |   | 12/1993 | Clark ............................. 514/8  |
| 5,686,423 | A |   | 11/1997 | Wang ............................ 514/18 |
| 5,762,922 | A | * | 6/1998  | Noble et al. ................ 424/85.4  |
| 5,804,550 | A |   | 9/1998  | Bourguignon .................. 514/3  |
| 6,187,906 | B1 | * | 2/2001  | Gluckman et al. ........... 530/331 |

FOREIGN PATENT DOCUMENTS

| EP | 0/366638 | 5/1990 |
| WO | 93/02695 | 2/1993 |
| WO | 93/21216 | 10/1993 |
| WO | WO 95/17204 | 6/1995 |
| WO | WO 98/14202 | 4/1998 |
| WO | WO 99/65509 | 12/1999 |

OTHER PUBLICATIONS

J. Rudinger, "Peptide Hormones" (Ed. JA Parsons, Jun. 1976) pp. 1–6.*

Guan et al., *The Effects of IGF–1 Treatment After Hypoxic–Ischemic Brian Injury In Adult Rats*, The Journal of Cerebral Blood Flow and Metabolism, vol. 13 (1993), pp. 13:609–616.

G. M. Shepherd, "Neurotransmitters and Neuromodulators", Neurobiology Second Edition (1988), pp. 145–176.

Curtis D. R. et al., "Amino Acid Transmitters In The Mammalian Central Nervous System", Ergebnisse Der Physiologie, vol. 69 (1974), pp. 97–188.

V. Sara, et al, "*Identification of GLY–PRO–GLU (GPE), The Aminoterminal Tripeptide Of Insulin–Like Growth Factor 1 Which Is Truncated In Brain, As A Novel Neuroactive Peptide*", Biochemical & Biophysical Research Communications vol. 165, No. 2, 1989, Dec. 15, 1989 pp 766–771.

L. Nilsson–Hakansson, et al., "*Effects of IGF–1, Truncated IGF–1 And The Tripeptide Gly–Pro–Glu On Acetylcholine Release From Parietal Cortex Of Rat Brain*", Neuroreport, 4,1111–1114(1993).

J. Saura, "*Neuroprotective Effects Of Gly–Pro–Glu, the N–terminal Tripeptide Of IGF–1, In The Hippocampus In Vitro*", Neuroreport 10, pp. 161–164 (1999).

V. Sara, "*The Biological Role of Truncated Insulin–Like Growth Factor–1 and The Tripeptide GPE In The Central Nervous System*", Annals of the New York Academy of Sciences vol. 692, pp 183–191 (1998).

Sara, V. R. et al.: "The Biological Role of Truncated Insulin–Like Growth Factor–1 and The Tripeptide GPE In The Central Nervous System", Annals of the New York Academy of Sciences, vol. 692, pp. 183–191, (1991).

* cited by examiner

Primary Examiner—Bennett Celsa
(74) Attorney, Agent, or Firm—Fliesler Meyer LLP

(57) ABSTRACT

A method for treatment or prophylaxis of a patient suffering from functional symptoms of Parkinson's disease, especially as a consequence of damage to dopaminergic neurons, by administering to the patient a neuroprotective amount of a peptide selected from the tripeptide gly-pro-glu (GPE) and analogs and mimetics thereof, preferably GPE. The GPE will usually be administered subsequent to the onset of Parkinson's disease but prior to the damage of said dopaminergic neurons.

7 Claims, 4 Drawing Sheets

METHODS TO IMPROVE NEURAL OUTCOME

CROSS-REFERENCE TO RELATED APPLICATIONS

This application is a continuation-in-part of application Ser. No. 08/907,918, filed Aug. 11, 1997 now abandoned. Application Ser. No. 08/907,918 is a continuation of abandoned application Ser. No. 08/656,331, filed Jun. 14, 1996 now abandoned, application Ser. No. 08/656,331 is a 371 of PCT International Application No. PCT/NZ94/00143, filed Dec. 20, 1994. PCT International Application No. PCT/NZ94/00143 claims the priority under 35 USC 119 of New Zealand Applications Nos. 250,572, filed Dec. 23, 1993; 260091, filed Mar. 14, 1994; and 264,070, filed Jul. 22, 1994.

FIELD OF THE INVENTION

This invention relates to methods for the treatment or prevention of central nervous system (CNS) and peripheral nervous system cell damage in mammals and more particularly relates to a method of increasing the concentration of specified naturally occurring or introduced di- or tri-peptides within the central nervous system to treat the functional symptoms of an injury or disease affecting or liable to affect dopaminergic neurons.

BACKGROUND OF THE INVENTION

The central nervous system is peculiar among mammalian organs in that differentiated neurons are practically incapable of regeneration. Permanent loss of function is a likely outcome of a sufficiently severe injury to the brain. It is particularly sad to meet children whose brains have been damaged by hypoxia during a difficult birth. There is therefore a need for means to protect cells of the central nervous system (also including the glial cells) from death after an injury. After asphyxial, traumatic, toxic, infectious, degenerative, metabolic, ischemic or hypoxic insults to the central nervous system (CNS) of man or other mammals a certain degree of damage in several different cell types may result. For example periventricular leucomalacia, a lesion which affects the periventricular oligodendrocytes is generally considered to be a consequence of hypoxic ischemic injury to the developing preterm brain (Bejar et al., Am. J. Obstet. Gynecol., 159:357–363 (1988); Sinha et al., Arch. Dis. Child., 65:1017–1020 (1990); Young et al., Ann. Neurol., 12:445–448 (1982)). Damage to the CNS by trauma, asphyxia, ischemia, toxins or infection is frequent and may cause sensory, motor or cognitive deficits. Glial cells which are non-neuronal cells in the CNS are necessary for normal CNS function. Infarcts are a principal component of some hypoxic ischemic induced damage and loss of glial cells is an essential component of infarction. There appears to be a kind of "delayed injury process" in which apparently "self destructive" neural activity occurs some time after an injury; attempts to control this activity appear able to alleviate the effects of this delayed injury process. Disease of the CNS also may cause loss of specific populations of cells. For example Multiple Sclerosis is associated with loss of myelin and oligodendrocytes, similarly Parkinson's disease is associated with loss of dopaminergic neurons. Some situations in which CNS injury or disease can lead to predominant loss of neurons and/or other cell types include: perinatal asphyxia associated with fetal distress such as following abruption, cord occlusion or associated with intrauterine growth retardation; perinatal asphyxia associated with failure of adequate resuscitation or respiration; severe CNS insults associated with near-miss drowning, near miss cot death, carbon monoxide inhalation, ammonia or other gaseous intoxication, cardiac arrest, collapse, coma; meningitis, hypoglycemia and status epilepticus; episodes of cerebral asphyxia associated with coronary bypass surgery; cerebral anoxia or ischemia associated with stroke, hypotensive episodes and hypertensive crises; and cerebral trauma.

There are many other instances in which CNS injury or disease can cause damage to cells of the CNS. It is desirable to treat the injury in these instances. Also, it is desirable to prevent or reduce the amount of CNS damage which may be suffered as a result of induced cerebral asphyxia in situations such as cardiac bypass surgery.

We have previously shown (in U.S. Pat. No. 5,861,373) that the growth factor called insulin-like growth factor 1 (IGF-1) has an unanticipated action, namely to prevent brain cells from dying after an asphyxial or ischemic brain insult (Gluckman et al Biochem Biophys Res Commun 182:593–599 1992). Because insulin also has a neuroprotective action (Voll et al Neurology 41:423–428 (1991)) and insulin and IGF-1 can both bind to the IGF-1 receptor, it was generally assumed that this brain rescue mode of action of IGF-1 was mediated via the IGF-1 receptor (Guan et al J. Cereb. Blood Flow Metab. 13:609–616(1993)).

It is known that IGF-1 can be modified by proteolytic cleavage in nervous tissue to des-1–3N IGF-1, that is IGF-1 missing the 3 amino acids from the amino terminal of the molecule, and hence after cleavage there is also a 3 amino acid peptide gly-pro-glu which is the N terminal tripeptide. This tripeptide is also termed GPE. As des-1–3N IGF-1 also binds to the IGF-1 receptor and GPE does not, GPE was thought to be of no significance to the neuronal rescue action of IGF-1.

Our previous work had shown that the brain increases its production of IGF-1 following brain injury by hypoxia-ischemia and that in addition it increases the synthesis of two specific binding proteins, IGF binding protein-2 (IGFBP-2) and IGF binding protein-3 (IGFBP-3) (Gluckman et al Biochem Biophys Res Commun 182:593–599 (1992)) and Klemp et al Brain Res 18:55–61 (1992). These were hypothesized to attract the IGF-1 into the region of injury to reach concentrations necessary for neuronal rescue. For this reason IGF-1 was anticipated to be more potent given at a site distant from the injury than des-1–3 N IGF-1 which does not bind well to binding proteins. This was indeed the case—des-1–3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

The disclosures of all documents referred to in this application are incorporated herein by reference.

To date, there has been no enabling reference in the prior art to the manipulation of the cleaved tripeptide GPE itself to prevent or treat CNS injury or disease leading to CNS damage in vivo.

One disease which leads to CNS damage in vivo is Parkinson's disease. Parkinson's disease is the second most prevalent neurodegenerative disorder after Alzheimer's. It is a chronic and progressive motor system disorder and is distinguished by a tremor at rest, muscular rigidity, a slowness of movement initiation and movement execution and a mask-like appearance to the face.

The cause of this disease is unknown but the symptoms are a consequence of an 80% or greater loss of dopaminergic neurons (which produce dopamine) in the pars compacta region of the substantia nigra.

SUMMARY OF THE INVENTION

It is an object of the invention to provide a method for treating functional symptoms as a consequence of damage to dopaminergic neurons from Parkinson's disease.

Accordingly, in a broad aspect the invention comprises a method for treating functional symptoms as a consequence of damage to dopaminergic neurons from Parkinson's disease comprising the step of administering to said patient a neuroprotective amount of a peptide selected from the tripeptide gly-pro-glu (GPE) and analogs and mimetics thereof.

Preferably, the peptide administered is GPE. The GPE will usually be administered subsequent to the onset of Parkinson's disease but prior to the damage of said dopaminergic neurons.

Conveniently, GPE is administered in the form of a pharmaceutical composition including a pharmaceutically acceptable carrier therefor.

GPE can be administered directly to where the dopaminergic neurons to be protected are located, such as by being preferably administered directly to the brain or cerebrospinal fluid by cerebro-ventricular injection, by injection into the cerebral parenchyma or through a surgically inserted shunt into the lateral cerebral ventricle of the brain.

In one form, GPE is administered in combination with artificial cerebrospinal fluid. GPE can also be administered systemically for transport to where the dopaminergic neurons to be protected are located, such as by being administered through an intravenous, oral, rectal, nasal, subcutaneous, inhalation, intraperitoneal or intramuscular route.

It will be usual for the dosage range of GPE administered to be from about 1 $\mu$g to about 100 mg of GPE per kg of body weight in the mammal.

Although the present invention is defined broadly above, it will be appreciated by those skilled in the art that it is not limited thereto but includes embodiments of which the description provides examples.

BRIEF DESCRIPTION OF DRAWINGS

A better understanding of the invention will be gained from reference to the foregoing examples and drawings where.

DETAILED DESCRIPTION OF THE INVENTION

Figure 1:
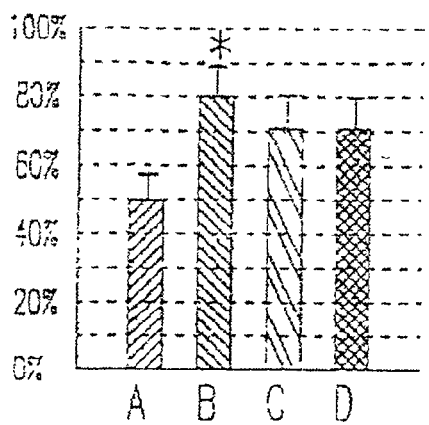
FIG. 1 shows the incidence of cortical infarction following treatment with vehicle alone, 50 $\mu$g of IGF-1, the NMDA antagonist MK801 (1 mg), or IGF-1 plus MK801 2 hours after the hypoxia. Similar to previous studies the incidence of cortical infarction was lower in the IGF-1 treated group, whereas MK801 had a lesser effect.

We have explored the observation that insulin-like growth factor 1 (IGF-1) appears to be modified by proteolytic cleavage in nervous tissue to des-1–3N IGF-1, that is IGF-1 missing the 3 amino acids from the amino terminal of the molecules, and to a 3 amino acid peptide gly-pro-glu (GPE) which is the N terminal tripeptide. As des-1–3N IGF-1 also binds to the IGF-1 receptor and GPE does not, GPE was thought to be of no significance to the neuronal rescue action of IGF-1. Surprisingly, GPE is effective.

Our previous work had shown that the brain increases its production of IGF-1 following brain injury by hypoxiaischemia and that in addition it increases the synthesis of two specific binding proteins, IGF binding protein-2 (IGFBP-2) and IGF binding protein-3 (IGFBP-3) (Gluckman et al Biochem Biophys Res Commun 182:593–599 1992) and Klemp et al Brain Res 18:55–61 (1992). These were hypothesized to attract the IGF-1 into the region of injury to reach concentrations necessary for neuronal rescue. For this reason IGF-1 was anticipated to be more potent given at a site distant from the injury than des-1–3 N IGF-1 which does not bind well to the binding proteins. This was indeed the case—des-1–3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

To date, there has been no enabling reference in the prior art to the manipulation of GPE to prevent or treat CNS injury or disease leading to CNS damage in vivo.

Surprisingly we have found that GPE itself appears to be the compound that underlies the phenomenon of neural rescue (see for instance Example 3). This has led us to propose that treating a patient for neural injury or disease with IGF-1 is a less soundly based proposition, as a tripeptide is easier to prepare, and as it is a more mobile and less immunologically challenging compound therefore it can be expected to be more effective.

Sara patent EP 0366638A2 suggested that GPE could act as a neuromodulator to alter the activity of neuronal cells. Because it contains a glutamate and a glycine she suggested that it is likely to act at a NMDA class of receptor either as a partial agonist or antagonist. The classical NMDA receptor antagonist is MK801. We therefore compared the action of IGF-1 to MK801 given after injury and also looked for any additive effect.

Experiment 1 in our specification is a non-limiting example to show that in rats subject to hypoxic-ischemic injury the action of IGF-1 is not mimicked by or added to by use of an NMDA receptor antagonist. This study shows that IGF-1 does not act by means of an action to modulate NMDA mediated neuronal activity in terms of hormone release and thus there was no prior art to suggest that IGF-1 might act as a prohormone to form GPE which in turn stops neurons dying. Rather, the prior art suggest that IGF-1 acts via the IGF-1 receptors.

Experiment 2 is a non-limiting example in fetal sheep to show that IGF-1, which induced neuronal rescue in an ischemic model in fetal sheep, did not suppress cortical electroencephalographic activity whereas MK801 does so (Tan et al Ann Neurol 32:677–682 (1992)).

Experiment 3 is a non-limiting example which shows that despite the prior art suggesting that IGF-1 acts as a neural rescue agent via the IGF-1 receptor without modulating neuronal activity, GPE was as potent as a neuronal rescue agent as was IGF-1. The GPE was given shortly after the hypoxic ischemic injury but before degradation of DNA occurs in the regions which are destined in control animals to show neuronal death. The reduced degree of hippocampal neuronal loss and cortical infarction which is a reflection of less neuronal and less glial cell loss due to asphyxia. The mechanism by which GPE leads to prevention of cell death is not known but is clearly not by modulating neuronal activity.

Experiment 4 is a non-limiting example in 21-day old rats to show that GPE has a significant beneficial effect on neuronal outcome when given intraperitoneally, two hours after an insult comprising hypoxia.

Sara has shown GPE to modulate neuronal activity and, because agents such as NMDA which do, may have some role in treating neuronal injury, suggested but did not provide any evidence for its use as a treatment for neurological disease. However there is no prior art for our claims which are that GPE can be used to prevent neurological disease by preventing neurons and glia from dying. The type of clinical application of which our invention is directed is totally different from Sara.

More recent work by us tends to support the finding that the effects of GPE are most developed in the hippocampus itself, the CA1–2 regions. Thus our data relating to GPE and the like may be in the first instance most relevant to disease primarily involving the hippocampus, and in the second instance to other populations of neurons once the modus operandi is better understood.

The invention relates to a method of manipulating neural damage. In a first aspect, the invention relates to a method of treating CNS damage after an injury to the CNS occurs. For example, the patient may have suffered perinatal asphyxia or asphyxia or cerebral ischemia associated with a stroke or other non-limiting examples of CNS injuries having been described earlier herein. In these instances, it is desirable to reduce or eliminate the symptoms of CNS damage.

CNS damage may for example be measured clinically by the degree of permanent neurological deficit cognitive function, and/or propensity to seizure disorders. (In our experiments we have used histological techniques).

It is proposed that the concentration of GPE and/or analogues thereof in the CNS and in the brain of the patient in particular should be increased in order to treat the CNS damage. Accordingly, GPE and/or analogues thereof can be administered directly to the patient. By the term "GPE" we refer in particular to gly-pro-glu or gly-pro or pro-glu, especially gly-pro-glu. By analogues of GPE is meant compounds which exert a similar biological effect to GPE. These compounds can be derived from humans or other animals. GPE and analogues can be purified from natural sources or produced by synthetic techniques. Synthetic GPE can be obtained commercially.

Alternatively, compounds can be administered which, upon administration to the patient, increase the active concentration of GPE and/or naturally occurring analogues thereof in the CNS. By "active concentration" is meant the biological concentration of GPE and/or analogues in the CNS of the patient able to exert an effect on CNS damage. For example, elevating the active concentration of IGF-1 may enhance the formation of GPE.

GPE, analogues therefore and compounds which elevate the active concentrations thereof can be administered centrally or systemically. Desirably, the compositions are administered directly to the CNS of the patient. Accordingly, the compositions may be administered directly into the brain or cerebrospinal fluid by techniques including lateral ventricular through a burrhole, or anterior fontanelle, lumbar or cisternal puncture or the like.

If desired, a combination of the compounds can be administered. In addition they may be re-administered with other agents or growth factors, for example, transforming growth factor beta (TGF-β).

The foregoing experiments show that the expression of IGF-1 after a neural insult follows a specified time course and occurs in specified areas of the body. Accordingly, the compositions should be administered according to the pattern of CNS injury and the elapsed time subsequent to an injury so as to produce the most desirable results. The compositions may be administered directly to the region of the body where the greatest CNS injury has occurred.

The compositions may for example be administered about 0.5 to 100 hours after an injury and only one treatment may be necessary. Alternatively, repeated treatment may be given to the patient.

A suitable dosage range may for example be between about 0.1 to 1000 µg of GPE (and/or analogues or compounds that elevate the concentrations thereof) per 100 g of body weight where the composition is administered centrally.

The treatment may be given before (as well as after) an injury—as for example before elective surgery. Examples of relevant elective procedures include neural surgery, in which retraction of lobes of the brain may lead to cerebral edema, or heart operations, such as valve replacement, in which inevitable small emboli are said to lead to detectable impairment of brain function in some 75% of cases.

The invention also relates to a medicament for treating CNS injury. The medicament can comprise GPE and/or analogues thereof and/or peptidomimetics thereof or a compound which elevates the concentration of GPE in the CNS such as IGF-1. The compounds are desirably provided in a pharmaceutically acceptable carrier or diluent such as those known in the art. GPE, analogues, peptidomimetics and compounds that elevate the concentration thereof can be manufactured by peptide synthesis techniques. Alternatively, the compounds can be isolated from natural resources.

A compound with little or no immunological effect may be administered over long periods, as long as other side effects prove to be unimportant. We propose that oral doses of a pharmaceutical compound promoting higher GPE levels in the brain (such as GPE itself) may be given over long periods to (for example) sufferers from chronic CNS disturbances such as Parkinson's disease, multiple sclerosis, Alzheimer's disease, and the like. In this instance the tripeptide nature of GPE should allow its entry into the circulation by direct absorption from the buccal mucosa from a lozenge placed under the tongue. We have shown that GPE is effective by intraperitoneal administration (in young rats) so it is at least not limited to injection into the CSF. The efficacy of GPE therapy in such disease may be difficult to establish unless clinical trials are attempted.

The invention is supported by the following experimental data. In the following studies it was found that:

The neuronal rescue effect of IGF-1 is not mimicked or added to by use of an NMDA receptor antagonist.

Unlike an NMDA receptor antagonist neuronal rescue therapy with IGF-1 does not suppress seizure activity. Thus, the neuronal rescue effects of treatment with IGF-1 are not primarily mediated via the NMDA receptor.

Alterations in CNS levels of the N terminal tripeptide of IGF-1 called GPE can alter CNS damage resulting as a consequence of an injury to the CNS. GPE is effective in reducing clinical symptoms in animal models of Parkinson's disease which makes GPE suitable for use in treating Parkinson's disease.

The present invention is further illustrated by the following Experiments and Examples. These are offered by way of illustration only and are not intended to limit the invention in any manner. The studies described were approved by the Animal Ethical Committee of the University of Auckland.

Experiment 1

The objective of this study was to compare the effects of administering IGF-1 and the NMDA receptor antagonist MK801 after a CNS injury in order to clarify the site of action of IGF-1. The experiments involved treating the rats with vehicle, IGF-1, MK801 or IGF-1 plus MK801 2 hours after a CNS injury. These rats had an hypoxic-ischemic injury to one cerebral hemisphere induced in a standard manner. One carotid artery was ligated and the animal was subjected two hours later to a defined period of inhalational hypoxia. The degree, length of hypoxia, ambient temperature and humidity were defined to standardize the degree of damage. They were sacrificed five days later for histological analysis using stains (acid-fuchsin) specific for necrotic neurons. In such experiments cell death typically is restricted to the side of the side of arterial ligation and is primarily in the hippocampus, dentate gyrus and lateral cortex of the ligated hemisphere.

Adult Wistar rats (68 280–320 g) were prepared under 3% halothane/$O_2$ anesthesia. The right side carotid artery was ligated. A guide cannula was placed on the dura 8.2 mm anterior from bregma and 1.4 mm from midline on the right. The rats were allowed to recover from anesthesia for 1 hour and were then placed in an incubator with humidity 85±5% and temperature 34±0.5° C. for 1 hour before hypoxia. Oxygen concentration was reduced and maintained at 6±0.2% $O_2$ hypoxia for 10 minutes. The rats were kept in the incubator for two hours after the hypoxia and then treated either with IGF-1 (n=17), MK801 (n=17), MK801 plus IGF-1 (n=17) or vehicle (n=17) alone. Fifty micrograms of IGF-1 or vehicle alone (0.1% BSA in 0.15M PBS (pH 7.3)) were given via intra-ventricular (IVC) infusion. Simultaneously the rats were treated subcutaneously (IP) using 1 mg MK801/0.5 ml or saline alone. The intraventricular injections of 50 $\mu$g IGF-1 or vehicle alone were made into the right lateral ventricle at 1 $\mu$l/minute under 1.5%–2% halothane anaesthetic. Rats in each treatment group were infused simultaneously. The rats had free access to food during experiment and were euthanized at 120 hours after hypoxia with overdose of sodium pentobarbitol. Briefly, the brain was perfused in-situ with FAM (formaldehyde, acetic acid, methanol 1:1:8) then paraffin embedded. The sections were stained with thionin and acid fuchsin. The presence of cortical infarction, defined as a region of tissue death or parenchymal pan-necrosis due to death of glia as well as neurons, was determined via light microscopy by an assessor who was blinded to the experimental groupings.

Results are illustrated in FIG. 1, showing the ratio between the R (ligated carotid) and L sides of the brains, wherein column A is vehicle, column B is 50 $\mu$g IGF-1, column C is 1 mg MK801, and column D is 50 $\mu$g IGF-1 with 1 mg MK801. (p(*)=0.031).

Similar to previous studies by ourselves the incidence of cortical infarction was lower following IGF-1 treatment (33%) compared to 65% in controls (Guan et al J Cereb Blood Flow Metab 13:609–616 (1993)); whereas following MK801 treatment the incidence was 50%. The combination of IGF-1 and MK801 was 41%. Thus in rats subject to hypoxic-ischemic injury the action of IGF-1 is not mimicked by or added to by use of NMDA receptor antagonist.

Experiment 2

The objective of this study was to compare the effects of treatment either with IGF-1 (see FIG. 2) and previously published work with the NMDA antagonist MK801 after an ischemic brain injury on postischemic seizures and neuronal losses in fetal sheep (Tan et al Ann Neurol 32:677–682 (1992)).

The methods were those of an earlier study (Tan et al Ann Neurol 32:677–682 (1992)). Briefly, late gestation fetal sheep were chronically instrumented to record EEG, nuchal activity and blood pressure, and were then returned to the uterus. Cortical EEG activity, nuchal activity and blood pressure were recorded throughout the experiment and the fetal brain subjected to 30 minutes of ischemia. Two hours later they were treated by an infusion of either 1 $\mu$g IGF-1 (n=6) or vehicle (artificial CSF) (n=6) into the lateral ventricle. Five days later the brains were fixed and assessed for neuronal loss as described previously (Tan et al Ann Neurol 32: 677–682 (1992)).

Figure 2:
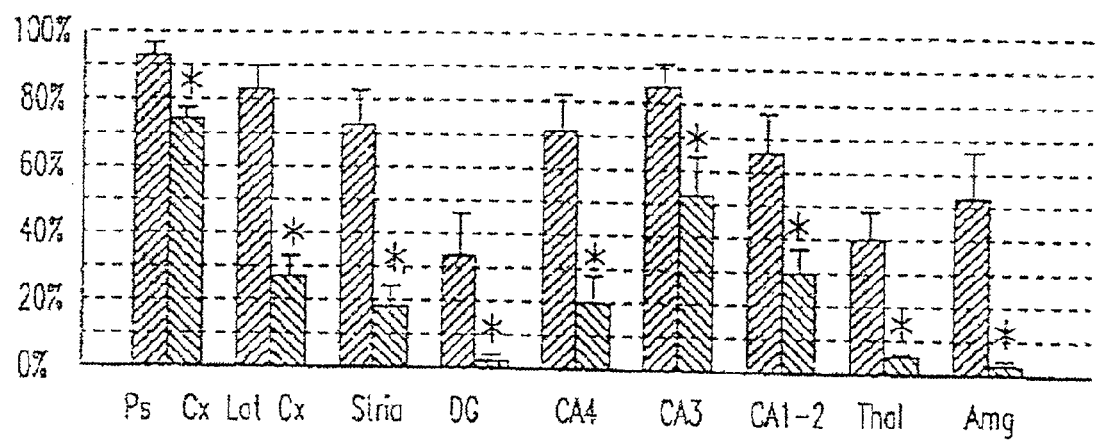
FIG. 2 shows an example of the effects of treatment with 1 $\mu$g IGF-1 2 h after an ischemia in fetal sheep. The names under the horizontal axis are standard abbreviations for various portions of the brain. This dose was neuroprotective but, unlike MK801, did not suppress seizures.

FIG. 2 shows the neuronal loss scores for a number of regions of the brain (identified by abbreviations on the horizontal axis) as a percentage of the untreated side. In all cases the ventricle is the left-hand column and the effects of 1 $\mu$g if IGF-1 is on the right.

The results show that, unlike the NMDA antagonist treated sheep, where electrical activity was markedly suppressed (Tan et al Ann Neurol 32: 677–682 (1992)), IGF-1 rescued neurons (FIG. 2) but did not suppress the postischemic seizure activity in fetal sheep. This study also suggests that the neuroprotective effects of IGF-1 does not primarily occur via the NMDA receptor or altered electrical activity of the brain.

Experiment 3

The objective of this study was to compare the effects of treatment with GPE to that of vehicle given 2 hours after a hypoxic-ischemic brain injury.

The dose of 3 μg of GPE was chosen to be equivalent to that present in 50 μg of IGF-1 which has been previously been shown to be neuroprotective (Guan et al J Cereb Blood Flow Metab. 13:609–616 (1993)). Unilateral hypoxic-ischemic injury was induced in adult 300±10 g male Wistar rats. The rats underwent unilateral carotid ligation under light halothane anesthesia.

Following one hour recovery they were placed in an incubator at 24° C. at 85±5% humidity for one hour before injury. They were subjected to 10 min inhalational asphyxia ($FiO_2$ 6.0%) and maintained in the incubator for one hour after asphyxia. Two hours after the termination of the inhalational injury, a single stereotaxically controlled lateral cerebroventricular injection of either 3 μg GPE (n=15) or phosphate buffered saline alone (n=15) was given. The animals were then maintained for 120 hrs, anaesthetized and the brains fixed in situ for histological assessment.

Figure 3:
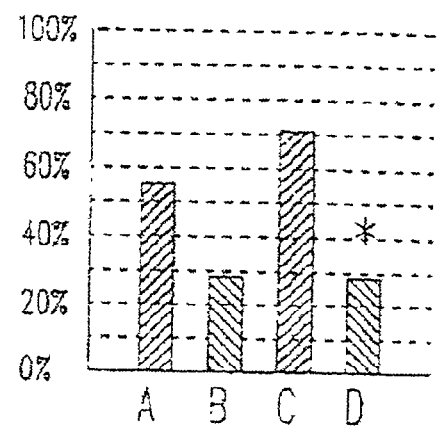
FIG. 3 shows the incidence of cortical infarction and hippocampal damage following treatment with 3 $\mu$g or vehicle 2 h after hypoxia. The incidence of hippocampal damage was reduced following treatment with 3 $\mu$g GPE*p<0.05.

Surviving and dead neurons were discriminated with the use of a thionin/acid fuchsin staining techniques [Williams et al Ped Res, (1990). Brown et al J. Neurol Sci, 16: 59–84 (1971)]. The results are shown in FIG. 3; using a scoring technique. It is evident that there was neuronal damage even on the unligated side, yet GPE therapy reduced the incidence of hippocampal damage in the ligated hemisphere compared to the vehicle treated controls ($p<0.05$ by Fisher's exact test). Similar to our previous study with IGF-1 the incidence of cortical infarction was lower following GPE treatment at 27% compared to the control/vehicle treated rats at 53% (Guan et al J Cereb Blood Flow Metab. 13:609–616 (1993)).

FIG. 3 shows the incidence of cortical infarction (columns A and B) and hippocampal damage (columns C and D) following treatment with vehicle (columns A and C) or 3 μg GPE (columns B and D) two hours after the hypoxia. The incidence of hippocampal damage was reduced following treatment with 3 μg GPE. The asterisk indicates a probability p of under <0.05.

Figure 4:
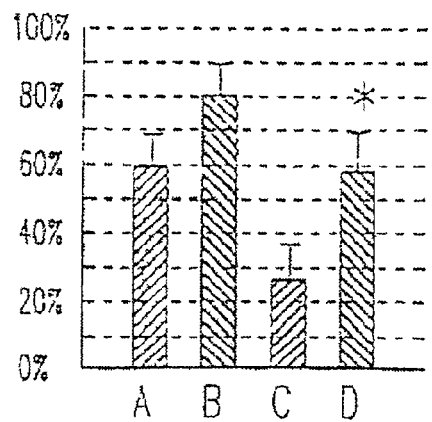
FIG. 4 shows results from the same experiment; wherein the two columns on the left show the area (hence volume, from stereology) of viable cortical tissue remaining after treatment, as a ratio between the right side of the brain and the left (injured) side, while the two columns labeled CA-1 show the proportion of live neurons remaining (comparing right and left sides) after the insult.

FIG. 4 shows a later, more critical assessment of the same experiment. For this figure the columns A and B indicate the proportional loss of area (which can be extrapolated to indicate volume using the well-known principles of stereology) between the left and right sides of the cortex of the brain, for either a control vehicle or 3 μg of GPE. Volumes were measured using computer-aided image analysis techniques. Columns C and D relate to the hippocampus and indicate the proportion of live neurons remaining after the experiment; again comparing right and left side counts. The asterisk indicates a probability of 0.04. Neurons were counted after staining, with the aid of a microscope. The administration of GPE has resulted in a significant reduction in the number of damaged cells. Thus a single central injection of GPE following an asphyxial injury in the adult rat was associated with a marked improvement in outcome as assessed histologically.

A histological experiment to locate GPE binding sites within the rat brain employed quantitative receptor autoradiography to locate [$^3$H]-GPE binding in coronal sections of the brain as previously described in Dragunow et al (1988, Brain Research 462, 252–257). Fresh frozen brain sections were cut on a cryostat and stored at −80° C. until use. Sections were then thawed and pre-incubated with 50 mM Tris HCl (pH 7.4) for 10 minutes at room temperature (250 μl per section). Sections were then dried and 250 μl per section of $5 \times 10^5$ counts/min of [$^3$H]-GPE also made up in Tris HCl buffer (50 mM, pH 7.4) was added for 1 hour at room temperature. Sections were then dried overnight at 4° C. and apposed to [$^3$H] sensitive film for 2 weeks, and then developed to produce autoradiograms.

Figure 6:
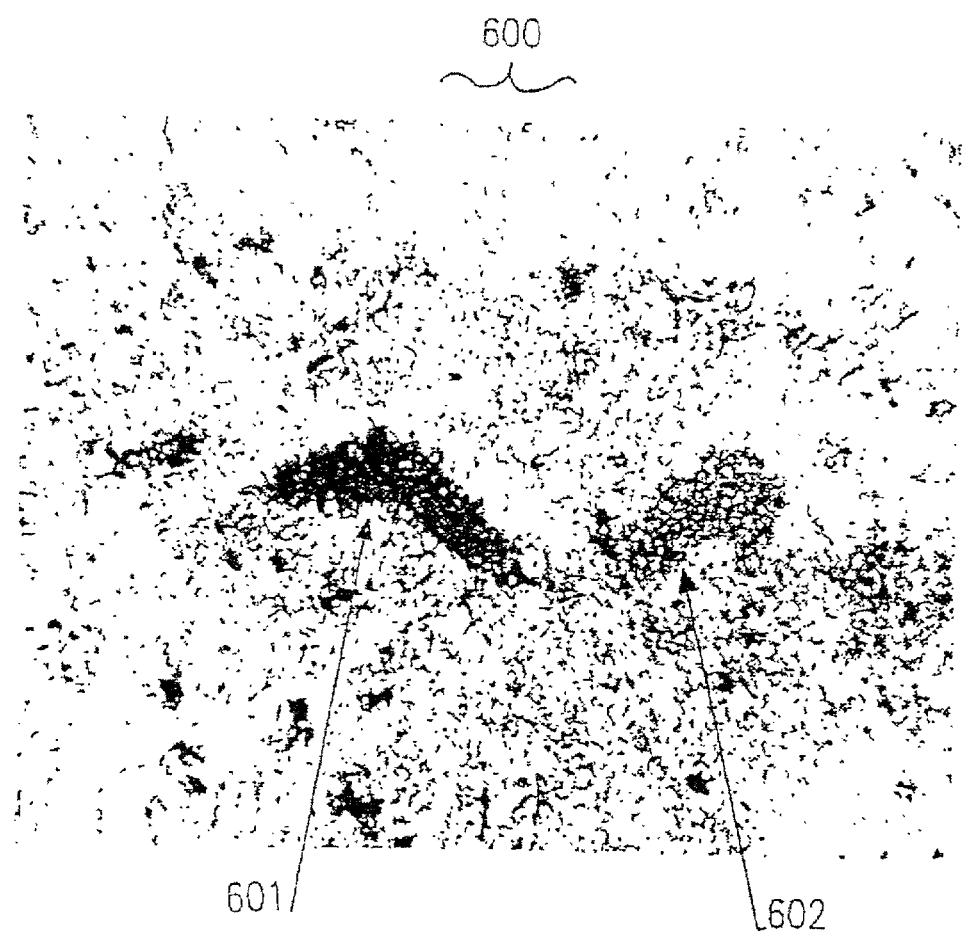
FIG. 6 is a photomicrograph which shows binding of GPE in an injured side of the hippocampus.
Figure 7:
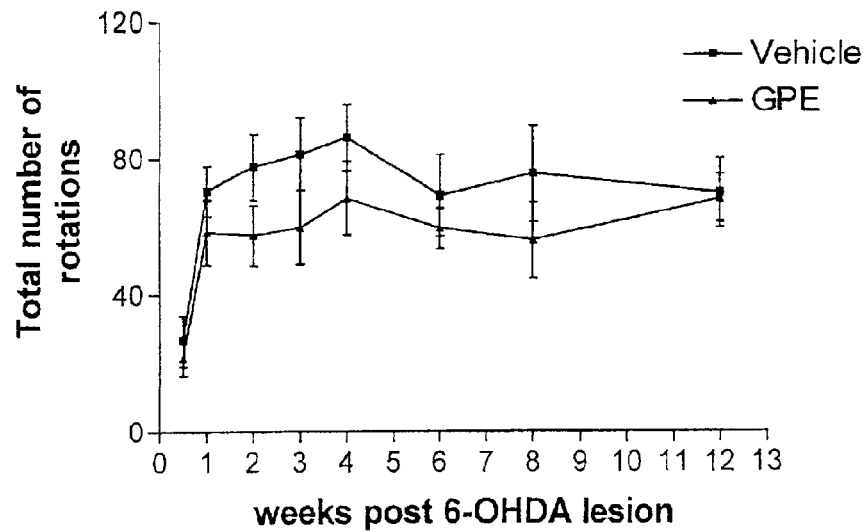
FIG. 7 shows total rotations/hour after a chemical 6-hydroxydopamine lesion and treatment with GPE or vehicle (p=0.01, n=10/group).
Figure 8:
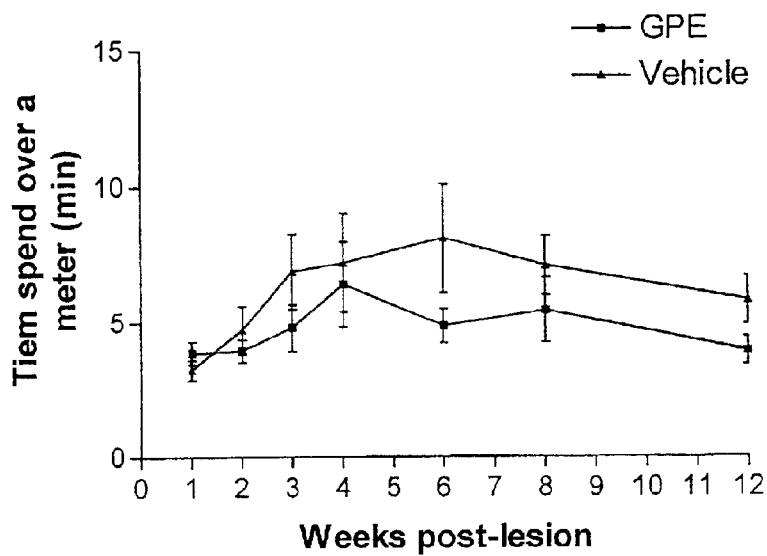
FIG. 8 shows the mean time taken to travel 1 meter±standard error (SE) after a chemical 6-hydroxydopamine lesion and treatment with GPE (n=11) or vehicle (n=8) (p=0.1).
Figure 9:
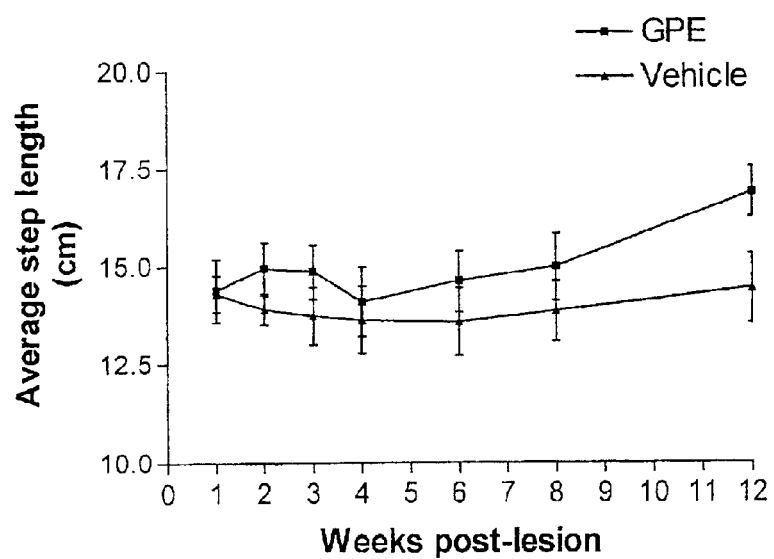
FIG. 9 shows the mean step length after a chemical 6-hydroxydopamine lesion and treatment with GPE (n=11) or vehicle (n=8) (p=0.1).
Figure 10:
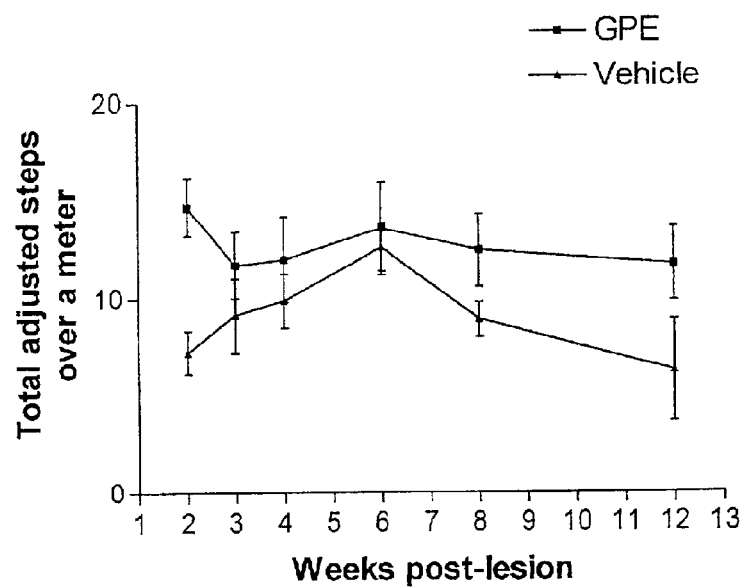
FIG. 10 shows the mean number of adjusting steps±SE after a chemical 6-hydroxydopamine lesion and treatment with GPE (n=11) or vehicle (n=8) (p=0.1).

Results as illustrated in FIG. 6 shown that the left hippocampus has bound the radioactive material while the corresponding side on the right shows little reaction. The neurons on this side were absent due to a pre-existing injury. This radiograph illustrates a particular binding site for GPE and tends to support our belief that GPE provides particular benefit at this important nucleus.

Experiment 4
Experimental Design and Animal Preparation

A paired experimental design was used and the experimenter was blind to the treatment groups. Twenty two male Wistar rats (280–310 g) were used for this study. After exposing the skull, 6-hydroxydopamine (6-OHDA) (8 μg in 2 μl 0.9% saline containing 1% ascorbic acid) was administered into the right medial forebrain bundle (MFB) using co-ordinates of AP +4.7 mm, R 1.6 mm, V −8 mm (Paxinos and Watson, 1982, New York: Academic Press) under 3% halothane anesthesia. The 6-OHDA was injected through a 25G needle connected by a polyethylene catheter to a 100 μl Hamilton syringe. The 6-OHDA was infused by a microdialysis infusion pump at a rate of 0.5 μl/min. The needle was left in the brain for a further 3 minutes before being slowly withdrawn. The skin was sutured with 2–0 silk and the rats were allowed to recover from the anesthesia. The rats were housed in a holding room with free access to food and water at all times except during functional testing.

Rotation Tests

At 3 days post-lesion, rats were injected with 0.1 mg/kg apomorphine and placed in yellow plastic bins. The number of contralateral rotations/minute were counted every 5 minutes for 1 hour. Animals were then paired for GPE or vehicle treatment according to the average number of turns/minute. Either GPE (1 mg in 0.1% BSA in 0.1 M PBS, Bachem) or its vehicle (0.1% BSA in 0.1 M PBS) were administered intraperitoneally 3 days post-lesion after the rotation test. Subsequent rotation tests were carried out at 1, 2, 3, 4, 8 and 12 weeks.

Stepping Tests

In addition, the day before each rotation test (starting 1 week post-lesion), stepping tests were carried out as a further measure of functional deficit after 6-OHDA lesion (Olsson et al. J. Neuroscience 15(5) 2149–2156, 1995; Kirik et al. Exp. Neurology 152 259–277, 1998).

Step Time and Step Length: Three days prior to surgery, rats were pre-trained to run along a plank of wood into their home cages. The three animals that did not receive pre-training were excluded from the analysis. Post-surgery recordings were made on day 3 post-lesion and subsequently a day before each rotation test. Before placing each rat on the plank (covered with paper) the front contralateral paw of the rat was dipped in Indian ink. Time taken for a rat to run a meter was measured by placing the rat on the plank at the start mark, then measuring the time it took for it to cross the 1 meter mark. Each animal was given 3 trial runs before 3 actual runs were recorded. The step-size of the front contralateral paw was measured by measuring the length between the paw prints made on the paper. The paper was changed between animals.

Adjusting Steps: The rat was held by the experimenter with one hand fixing the hindlimbs and the other hand fixing the ipsilateral paw with the contralateral paw touching the table, The contralateral paw was then dragged towards the ipsilateral side at a speed of 5–8 sec/meter and the number of adjusting steps counted.

Statistical Analysis

The data were analyzed using repeated measures analyses by the SAS statistical analysis package (SAS Institute Inc, Cary N.C., USA).

Results

Rotation Test

Three days after 6-OHDA lesion 17/20 rats exhibited contralateral rotations after apomorphine (average 122 turns/hour). The 3 rats that did not turn were excluded from the analysis. GPE treatment significantly decreased the number of contralateral rotations over the 12 weeks following treatment (p=0.01, FIG. 6).

Stepping Tests

GPE treatment significantly decreased the time taken to travel 1 meter over time (p=0.03, FIG. 2). GPE also significantly increased step length over time (p=0.01, FIG. 3). Further, GPE also significantly increased the number of adjusting steps in the contralateral paw (p=0.01, FIG. 4).

Conclusions

The above examples show the GPE administration is effective in reducing functional symptoms in the 6-OHDA rat lesion model of Parkinson's disease.

The examples also show that peripheral administration of GPE is effective in improving functional deficits in the 6-OHDA rat lesion model of Parkinson's disease.

Summary of Experiments

GPE (in these experiments, dissolved in 0.15 M phosphate buffered saline) administered in a single dose given in the period commencing with the time of the CNS injury through to about 8 hours thereafter (and including a time point of about 2 hours after the neural injury) has shown therapeutic effect in reducing or eliminating the severity of CNS damage suffered after a neural injury. GPE is especially useful in reducing neuronal loss, infarction, and loss of glial and other cells associated with CNS injury. Thus it can be seen that in at least the preferred forms of the invention a method and/or medicament for treating CNS damage is provided which is able to substantially prevent or treat CNS damage. CNS damage may be associated with asphyxia, hypoxia, toxins, infarction, ischemia or trauma. It will be appreciated that the main application of the invention is to humans. However, the usefulness of the invention is not limited thereto and treatment of other non-human animals, especially mammals is also within the scope of the invention.

The present invention, therefore, recognizes the role of an administration of a medicament comprising GPE and/or other compounds of similar effect into a patient at or following a CNS injury with the consequential result that CNS damage is minimized by preventing the otherwise consequential, self-induced damage that would occur following the injury, i.e. it is not involved with the repair of damage that has already occurred but to a treatment at, or subsequent, to the injury but before the consequential long term damage occurs thereby minimizing the occurrence of such damage.

EXAMPLE 1

Alleviation of Brain Damage to an Infant or Neonatal Mammal Resulting from Perinatal Asphyxia Basing the dose rates on our rat and fetal sheep models a suitable method for alleviation of brain damage is to infuse the infant's circulation by intravenous route with GPE or an analogue thereof in normal saline at a preferred dose rate in the range of 0.1 µg/kg to 10 mg/kg and more preferably about 1 mg/kg from within about 12 hrs of the onset of fetal distress until about 120 hrs later. A higher loading dose may be used at the commencement of treatment. Alternatively GPE may initially be administered via the maternal circulation in a higher intravenous dose rate of about 5 mg/kg, while the placenta is largely functional. Alternatively intraventricular infusion at about 10 µg/kg in artificial CSF into the lateral ventricle may be used as indicated.

EXAMPLE 2

Alleviation of Brain Damage to Human or Mammal Resulting from Stroke

Basing the dose rates on our rat and fetal sheep models a suitable method for alleviation of brain damage is to infuse the patients circulation by intravenous route with GPE or an analogue thereof in normal saline at a preferred dose rate in the range of 0.1 µg/kg to 10 mg/kg and more preferably about 1 mg/kg from within about 12 hrs of the onset of neurological signs until about 120 hrs later. A higher loading dose may be used at the commencement of treatment. Alternatively the same dose may be administered by close carotid injection. Alternatively intraventricular infusion at about 10 µg/kg in artificial CSF into the lateral ventricle may be used if indicated.

EXAMPLE 3

Alleviation of Brain Damage to Human and Mammal Resulting from Intracerebral Hemorrhage Basing the rates on our rat and fetal sheep models a suitable method for alleviation of brain damage is to infuse the patients circulation intravenous route with GPE or an analogue thereof or a peptidomimetic thereof in normal saline at a preferred dose rate in the range of 0.1 µg/kg to 10 mg/kg and more preferably about 1 mg/kg until about 120 hrs after the onset on the hemorrhage. A higher loading dose may be used at the commencement of treatment. Alternatively intraventricular infusion at about 10 µg/kg in artificial CSF into the lateral ventricle may be used.

EXAMPLE 4

Alleviation of Brain Damage to Human or Mammal Resulting from Traumatic Head Injury Basing the dose rates on our rat and fetal sheep models a suitable method for alleviation of brain damage is to infuse the infant's circulation by intravenous route with GPE or an analogue thereof or a peptidomimetic thereof in normal saline at a preferred dose rate in the range of 0.1 mg/kg to 10 mg/kg and preferably about 1 mg/kg from within about 12 hrs of the injury until about 120 hrs later. A higher loading dose may be used at the commencement of treatment. Alternatively intraventricular infusion at about 10 µg/kg in artificial CSF into the lateral ventricle may be used if indicated.

EXAMPLE 5

Peripheral Administration of GPE is Effective.

The object of this study was to compare the effects of treatment with GPE to that of a vehicle given 2 hours after an hypoxic-ischemic injury. The dose range of 2 µg to 200 µg was chosen to span a range of systemic doses that are greater than that required centrally (see experiment 3).

Unilateral hypoxic-ischemic injury was induced in 21 day old, 45±5 g Wistar rats. The rats underwent unilateral carotid ligation under light halothane anesthesia.

Following one hour recovery they were placed in an incubator at 34° C. 85±5% humidity for one hour before the injury. They were subjected to 1 min inhalation hypoxia (FiO$_2$ 8.0%) and then returned to room temperature (22° C.) and normoxia. Two hours after the termination of the injury, a single intraperitoneal injection of 0.25 ml of 2, 20 or 200 µg GPE per rat, or saline alone was given. The animals were then maintained for 120 hrs, anaesthetized and the brains were fixed for histological assessment.

Figure 5:
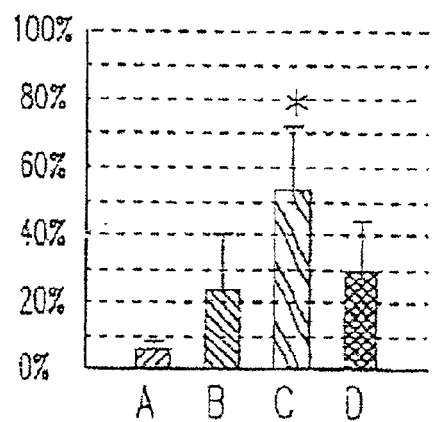
FIG. 5 shows the dose-response effect of GPE on neuronal outcome in the hippocampus (CA1–2 region), after peripheral (intraperitoneal) administration of GPE. The vertical axis shows the R/L ratio; the ratio between the unligated and the ligated sides of the brain.

Surviving and dead neurons were discriminated using the thionin/acid fuchsin staining technique (Guan et al J Cereb Blood Flow Metab. 13:609–616 (1993). The results, in which the height of a point is given by the ratio as a percentage of live neurons in the CA1–2 region on the right side to the number on the left side are shown in FIG. 5. Column A is vehicle, column B is 2 µg of GPE, column C is 20 µg of GPE, and column D is 200 µg of GPE. In this figure, the P value (0.031) was calculated by a method using one way ANOVA comparing many groups after Arcsin transformation.

GPE therapy (20 µg) reduced the loss of neurons in the CA1–2 regions of the hippocampus (p<0.05). Thus a single peripheral injection of GPE following an asphyxial injury in the rat was associated with a marked improvement in outcome as assessed histologically.

Options: Our choice of the intraperitoneal route was at least partly dictated by difficulty of any other routes in such small animals. While it is likely that the intraperitoneal route offers better access of GPE to the circulation and hence to the blood-brain barrier, other routes such as intravenous, intramuscular, or subcutaneous routes also appear to be available although the effective dose rate is likely to be greater.

The above experiment shows that the advantages of GPE over previously favored IGF-1 treatments include that it (unlike IGF-1) can cross the blood-brain barrier and so can gain access to the CNS from a peripheral site.

Pharmacology

Apart from the dose-response experiments on which FIG. 5 is based, we have not yet studied the pharmacological properties of GPE. We expect it to have a similar half-life in blood to other peptides; we expect that the liver and kidneys will relatively rapidly take up circulating GPE, and we expect that it has a relatively large therapeutic ratio. In view of the expected rapid uptake, intravenous administration is preferably in the form of steady state infusion.

Advantages

Some advantages offered by this invention, especially over IGF-1 and the like include: The active ingredients are easy to synthesize either in vitro or by other means such as recombinant techniques.

The small molecule can diffuse readily through the body and between compartments (e.g. the blood-brain barrier, and mucous membranes), aiding in the choice of methods for its administration and its ability to reach sites where injury has occurred. We have shown that intraperitoneal administration, to give one non-CSF example, is effective. The small molecule is unlikely to present a challenge to the immune system, so it may be administered over extended periods and it may be administered prophylactically.

Species differences are unlikely to be important.

In the specific case of Parkinson's disease, GPE is effective in reducing functional symptoms. GPE and its analogs and its mimetics therefore have specific application in treating disorders and diseases which affect dopaminergic neurons, particularly Parkinson's disease.

Although the present invention is defined broadly above, it will be appreciated by those skilled that it is not limited thereto but includes embodiments of which the description provides examples. Finally, it will be appreciated that various alterations and modifications may be made to the foregoing without departing from the scope of this invention as claimed.

We claim:

1. A method of treatment of a patient suffering from a functional symptom of Parkinson's disease, comprising administering an effective amount of GPE to said patient, wherein said functional symptom is tremor at rest, muscularrigidity, slowness of movement iniation, slowness of movement execution or mask-like appearance to the face.

2. The method of claim 1 where said functional symptom involves dopaminergic neurons.

3. The method of claim 1 where the said GPE is administered intravenously.

4. The method of claim 1 where the said GPE is administered via orally, rectally, nasally, subcutaneously, by inhalation, intraperitoneally or intramuscularly.

5. The method of claim 1 in which said GPE is administered to a patient suffering from Parkinson's disease who is in remission.

6. The method of claim 1 which is therapeutic.

7. The method of claim 1 where said functional symptom involves dopaminergic neurons within the substantia nigra of the CNS.

* * * * *